United States Patent
Fritsch

(10) Patent No.: US 11,903,795 B2
(45) Date of Patent: Feb. 20, 2024

(54) METHOD AND APPARATUS FOR TREATING A MALFORMED EUSTACHIAN TUBE

(71) Applicant: Domestic Legacy Limited Partnership, Indianapolis, IN (US)

(72) Inventor: Michael H Fritsch, Indianapolis, IN (US)

(73) Assignee: Ear Tech LLC, Indianapolis, IN (US)

( * ) Notice: Subject to any disclaimer, the term of this patent is extended or adjusted under 35 U.S.C. 154(b) by 45 days.

(21) Appl. No.: 16/137,317

(22) Filed: Sep. 20, 2018

(65) Prior Publication Data

US 2019/0083317 A1    Mar. 21, 2019

Related U.S. Application Data

(60) Provisional application No. 62/561,117, filed on Sep. 20, 2017.

(51) Int. Cl.
*A61M 29/02*      (2006.01)
*A61F 11/20*       (2022.01)
(Continued)

(52) U.S. Cl.
CPC ....... *A61F 11/202* (2022.01); *A61M 25/1002* (2013.01); *A61M 29/02* (2013.01);
(Continued)

(58) Field of Classification Search
CPC .. A61B 2018/00327; A61B 2017/3486; A61B 2017/22051; A61B 2017/22048;
(Continued)

(56) References Cited

U.S. PATENT DOCUMENTS 3,463,141 A * 8/1969 Mozolf ................. A61F 11/10
                                                128/842
3,734,100 A * 5/1973 Walker ............. A61M 25/1034
                                                128/207.15

(Continued)

OTHER PUBLICATIONS

Saab, Mark A., "Application of High Pressure Balloons in the Medical Device Industry", Medical Device and Diagnostic Industry Magazine, Sep. 2000.

(Continued)

*Primary Examiner* — Dianne Dornbusch
(74) *Attorney, Agent, or Firm* — Indiano Law Group, LLC; E. Victor Indiano; John T. Woods

(57) ABSTRACT

A balloon is provided for insertion into a mammalian eustachian tube. The balloon is a high pressure balloon having a body including a proximal end, a distal end, an exterior surface and an interior surface defining an air receivable interior. The body having a plurality of segments of different cross sectional areas, and a non-circular cross sectional profile. The balloon is inflatable between a deflated configuration and an inflated configuration. The body is sufficiently inelastic so as to be substantially incapable of expanding beyond a pre-determined size and shape when in the inflated configuration. The segments include a first segment having a first cross sectional area and a second segment disposed distally of the first segment The second segment has a second cross sectional area larger than the first cross sectional area.

17 Claims, 7 Drawing Sheets

(51) Int. Cl.
*A61M 25/10* (2013.01)
*A61B 18/00* (2006.01)

(52) U.S. Cl.
CPC ............. *A61B 2018/00327* (2013.01); *A61M 2210/0675* (2013.01)

(58) Field of Classification Search
CPC ...... A61F 11/002; A61F 11/10; A61F 11/202; A61F 11/20; A61M 25/1002; A61M 25/104; A61M 2210/0675; A61M 25/10–2025/1097; A61M 2210/0662; A61M 29/02; A61M 25/1004; A61M 2025/1004; A61M 2025/1088; A61M 2025/1086; A61M 2025/1075; A61M 2025/1072; A61M 2025/1059; A61M 2025/1054; A61M 2025/1052; A61M 2025/1047; A61M 2025/1045; A61M 2025/1043
See application file for complete search history.

(56) References Cited

U.S. PATENT DOCUMENTS

| | | | | |
|---|---|---|---|---|
| 4,190,033 A * | 2/1980 | Foti | .................... | A61B 5/4863 128/865 |
| 4,444,188 A * | 4/1984 | Bazell | ............. | A61M 25/10183 606/194 |
| 4,763,654 A * | 8/1988 | Jang | .................. | A61M 25/1011 604/101.01 |
| 5,752,522 A * | 5/1998 | Murphy | ............... | A61B 5/1076 600/505 |
| 5,954,740 A * | 9/1999 | Ravenscroft | ...... | A61M 25/1002 604/103.07 |
| 6,117,101 A * | 9/2000 | Diederich | ............. | A61B 18/00 604/22 |
| 6,589,286 B1 | 7/2003 | Litner | | |
| 6,607,545 B2 * | 8/2003 | Kammerer | ........ | A61M 25/1002 606/193 |
| 6,746,465 B2 * | 6/2004 | Diederich | ............. | A61M 25/10 604/101.02 |
| 7,833,282 B2 | 11/2010 | Mandape | | |
| 8,579,973 B2 | 11/2013 | Avior | | |
| 9,510,976 B2 | 12/2016 | Hossainy | | |
| 10,117,972 B2 * | 11/2018 | McClain | ................. | A61L 31/08 |
| 2005/0113687 A1 * | 5/2005 | Herweck | .............. | A61M 25/10 600/435 |
| 2007/0208301 A1 | 9/2007 | Evard et al. | | |
| 2007/0208310 A1 | 9/2007 | Evard et al. | | |
| 2009/0163890 A1 | 6/2009 | Clifford et al. | | |
| 2010/0036410 A1 * | 2/2010 | Krolik | ................ | A61M 25/1011 606/194 |
| 2010/0198191 A1 | 8/2010 | Clifford et al. | | |
| 2010/0274188 A1 * | 10/2010 | Chang | ...................... | A61B 8/12 606/167 |
| 2013/0274715 A1 * | 10/2013 | Chan | ...................... | A61B 17/22 604/514 |
| 2014/0031852 A1 * | 1/2014 | Edgren | .................. | A61B 17/24 606/199 |
| 2015/0202089 A1 * | 7/2015 | Campbell | .............. | A61B 1/233 600/478 |
| 2016/0213890 A1 * | 7/2016 | Kaufman | ............... | A61M 29/02 |

OTHER PUBLICATIONS

Mark A Saab, Applications of High Pressure Balloons in the Medical Device Industry, Medical Device and Diagostic Industry Magazine, Sep. 2000.

* cited by examiner

METHOD AND APPARATUS FOR TREATING A MALFORMED EUSTACHIAN TUBE

CLAIM OF PRIORITY

The instant application claims benefit of priority to Michael H. Fritsch, U.S. Provisional Patent Application No. 62/561,117, that was filed on 20 Sep. 2017 for a DEVICE FOR USE IN PERFORMING A EUSTACHIAN TUBE, which patent application is incorporated by reference herein in its entirety.

I. TECHNICAL FIELD OF THE INVENTION

The present invention relates to methods for treating diseases of the ear, and in particular, devices and methods for treating pathologies associated with the Eustachian tube of the ear.

II. BACKGROUND OF THE INVENTION

The Eustachian tube is also known as the auditory tube or the pharyngotympanic tube. The Eustachian tube links the Nasopharynx to the middle ear. It is a part of the middle ear, and in adult humans, is approximately 35 mm long.

The Eustachian tube extends at its lateral end, from the anterior wall of the middle ear to its medial end at the lateral ear of the Nasopharynx, as shown in FIGS. 1-3. The Eustachian tube meets the Nasopharynx approximately at the level of the inferior nasal concha. Approximately ⅓ of the tube that is closest to the middle ear is made of bone, with the rest of the tube being made of cartilage. The Eustachian tube raises a tubal elevation the torus tubarius, in the Nasopharynx where it opens.

Under normal conditions, the Eustachian tube is closed. However, it can be opened to allow a small amount of air to pass through the Eustachian tube to prevent damage to the ear, by equalizing pressures between the middle ear and the atmosphere, so that pressure is equalized on both sides of the tympanic membrane. Pressure differences between atmosphere and the middle ear can cause temporary conductive hearing loss by decreasing the motion of the tympanic membrane and ossicles of the ear.

Various methods of ear clearing such as yawning, swallowing or chewing gum may be used intentionally to open the tube and equalize pressures. When this happens, humans hear small popping sounds. Anyone who has experienced a change in ambient pressure caused by a change in elevation, such as occurs when riding an elevator in a very tall building, has likely, at one time or another, heard their "ears pop".

Another function served by the Eustachian tube is that it helps to drain mucous from the middle ear. Upper respiratory tract infections or allergies can cause the Eustachian tube or the membrane surrounding its opening to become swollen, thereby trapping fluid that serves as a growth medium for bacteria causing ear infections. This swelling can be reduced through the use of systemic pseudoephedrine, or topical oxymetazoline.

Ear infections are common in some children because the Eustachian tube is not fully functional. Additionally, since the Eustachian tube has a smaller diameter in children, the movement of air within the Eustachian tube becomes more difficult, thus making the Eustachian tube more susceptible to clogging. Further, the not-yet-fully-developed nature of children's immune systems, along with their poor hygiene habits often makes children more prone to upper respiratory infections than adults.

Some persons are born with a dysfunctional Eustachian tube, that is much narrower (has a smaller interior cross sectional area) than the typical sized Eustachian tube. Although the cause of this dysfunctional Eustachian tube may be genetic, it has also been suggested to be a condition in which the patient did not fully recover from the effects of pressure on the middle ear during birth. This disorder may result in a large amount of mucus accumulating in the middle ear, which often impairs hearing to a degree. For a variety of other reasons, a person may have a deformed Eustachian tube or otherwise may have a Eustachian tube having too small of an interior diameter, to properly enable the Eustachian tube to serve its function of draining mucus from the middle ear without becoming clogged and to otherwise be unable to prevent sufficient air to flow through the Eustachian tube so as to help to equalize pressure between the middle ear and atmosphere.

It is therefore one object of the present invention to provide a device and methodology for permitting a medical practitioner to treat conditions of the Eustachian tube, to help to restore the Eustachian tube to an appropriate size, shape and condition of openness to permit the flow of air and mucus therein, so as to both enable the Eustachian tube to properly drain mucus from the middle ear, and also to properly enable the Eustachian tube to equalize air pressure between the middle ear and the atmospheric pressure found in the auditory canal.

The need to uncollapse the Eustachian tube has been recognized in the art. In order to uncollapse and expand a Eustachian tube to a larger, better functioning cross sectional area, the current practice is to insert a cylindrical, high-pressure balloon into the Eustachian tube. The cylindrical high-pressure balloons that are currently used are all adult sized, as the operation at this time is only performed on adults. The cylindrical balloons that are used today currently have a diameter of between about 5 and 7 mm or some fixed and constant diameter somewhere there between. The ear surgeon chooses a particular balloon to be used based on the size of the Eustachian tube, that has some relation to the size of the person or the head of the person. When determining size, it is also important to factor in the age of the patient.

The sizes of the Eustachian tubes discussed above would not function well on children, as the Eustachian tubes of children likely have a smaller cross sectional area than adults. However, currently such procedures are not being done on children because they are believed at the present time to create too much of a medical-legal risk. However, it is expected that these procedures will ultimately be used on children, since children have the potential to show the greatest long term improvement and long term benefit by having their Eustachian tubes dilated to their appropriate cross sectional area when they are young.

Although cylindrical tubes are capable of performing their intended function, room for improvement exists. In particular, one problem with current cylindrical tubes is that since the cylindrical tubes do not conform to the natural shape of the Eustachian tube, currently used cylindrical tubes are likely to slip out of the Eustachian tube upon inflation, thus requiring the surgeon to re-insert the tubes back into the Eustachian tube and re-inflate the tubes to try again to expand the Eustachian tube.

Another problem that exists with currently used cylindrical tubes is that they have the potential to cause injury, such as the tearing of the Eustachian tube tissue. This tearing occurs because a cylindrical tubes generally have a constant diameter throughout the length. The use of a cylindrical balloon having a constant diameter that is inserted through a relatively smaller diameter portion of the Eustachian tube will exert a greater radially outwardly directed force on the tissue on that relatively narrower area, thus leading to a greater potential of tearing tissue.

The Eustachian tube has a cross-section that can best be described as something of an irregular ellipse. In particular, the cross-sectional height (diameter) of the Eustachian tube is significantly greater than the cross-sectional width of the Eustachian tube. Because of this, the insertion of a cylindrical balloon into such an irregular ellipse will have the potential to cause problems because greater pressure will be exerted on the lateral walls in the short, small width portions, and less pressure exerted on the top and bottom surfaces. This may cause insufficient dilation of the top and bottom and cause over the dilation of the lateral walls.

III. SUMMARY OF THE INVENTION

In accordance with the present invention, a balloon is provided for insertion into a mammalian eustachian tube. The balloon comprises a high pressure balloon having a body including a proximal end, a distal end, an exterior surface and an interior surface defining an air receivable interior. The body has a plurality of segments of different cross sectional areas, and a non-circular cross sectional profile. The balloon is inflatable between a deflated configuration and an inflated configuration. The body is sufficiently inelastic so as to be substantially incapable of expanding beyond a pre-determined size and shape when in the inflated configuration. The segments include a first segment having a first cross sectional area and a second segment disposed distally of the first segment The second segment has a second cross sectional area larger than the first cross sectional area.

In a preferred embodiment, the balloon has a height dimension and a width dimension. In the inflated configuration the height dimension is different than the width dimension. A guide member can be provided that has a distal end disposed adjacent to the distal end of the balloon, and a balloon engaging portion that extends through the balloon and out of the proximal end of the balloon, and a proximal portion having a length sufficient to include a proximal end that can be positioned exteriorly of a patient's nasal cavity when the balloon is positioned in the Eustachian tube.

The proximal portion of the guide member is preferably configured to receive an air source, and includes a passageway for conducting air to the balloon portion of the guide member. The balloon portion of the guide member includes apertures for conducting air between the interior of the balloon and guide member for permitting inflation and deflation of the balloon.

Additionally, the Eustachian tube of the mammal includes a plurality of segments having different cross sectional areas and different cross sectional profiles, including a first tube segment having a first height and first width different than the first height; and a second tube segment having a second height and second width different than the second height. Additionally, the first height and width are different than the second height and width.

The balloon segment has a cross sectional profile similar to the cross sectional profile of the first tube segment. When in the inflated configuration, the first balloon segment has a cross sectional area greater than the cross sectional area of the first tube segment prior to the inflation of the balloon.

In a most preferred embodiment, the balloon is sized and configured to exert an outwardly directed force on the Eustachian tube when in the inflated configuration. This outwardly directed force exerted by the first balloon segment on the first tube segment is generally equal to the force exerted by the second balloon segment on the second tube segment. Further, the Eustachian tube can include upper and lower wall portions, and first and second side wall portions. The first segment of the balloon is configured to exert a generally equal pressure on each of the upper wall portion, the lower wall portion, first side wall portion and second side wall portion when the balloon is inflated into the inflated configuration.

One feature of the present invention is that the varying cross-sectional area Eustachian tube balloon of the present invention enables the balloon to more closely conform to the actual natural shape of a properly shaped and sized normal Eustachian tube, to thereby better enable the surgeon to employ the balloon to correct deformities in the Eustachian tube and to open the Eustachian tube to an appropriate cross sectional area at various positions along the Eustachian tube.

Another feature of the present invention is that the tube comprises a high pressure balloon having a substantially fixed inflated geometry. This feature has the advantage of enabling the balloon to assume a fixed size, shape and geometry when inflated, which thereby helps to prevent the balloon from enlarging the Eustachian tube too much.

Also in accordance with the present invention, a method is provided for correcting deformities in at least a portion of a mammalian Eustachian tube. The method comprises providing a high pressure balloon for insertion into a mammalian Eustachian tube. The balloon has a proximal end, a distal end, an exterior surface and an interior surface that defines an ear receiving interior. The body has a plurality of segment of differing cross sectional areas, and a non-circular cross sectional profile. The balloon is inflatable between a deflated configuration and a inflated configuration.

The segments include a first segment having a first cross sectional area and a second segment disposed distally of the first segment. The second segment has a second cross sectional area larger than the first cross sectional area.

The balloon is inserted into a mammalian Eustachian tube. An air source is provided, and is used to inflate the balloon to a predetermined size by exerting a pressure on a first Eustachian tube segment that is positioned adjacent to the first balloon segment, that is generally equal to a pressure exerted on a second Eustachian tube segment by the second balloon segment.

Preferably, the balloon is insertable into a Eustachian tube such that the distal end of a balloon is placed relatively near the isthmus of the Eustachian tube of the patient, and the proximal end is placed relatively nearer the nasopharynx of the patient. The balloon is then inflated to an appropriate pressure, such as up to about 16 atmospheres (and preferably between about 5 and 12 atmospheres, and most preferably to about 10 atmospheres pressure), so that the balloon is moved from its collapsed configuration to its inflated configuration.

When in its inflated position, the balloon is designed to have a cross sectional area that is slightly larger than the cross section of the Eustachian tube, so that the balloon can exert a radially outwardly directed pressure against the walls of the Eustachian tube. Through the exertion of this pressure against the walls of the Eustachian tube, the cartilaginous walls of the Eustachian tube can be moved radially outwardly, to thereby expand the cross-sectional area of the passageway of the Eustachian tube.

The balloon is held in place within the Eustachian tube for a sufficiently long enough period of time, to permit the balloon to exert a sufficient force for a long enough time against the walls of the Eustachian tube, to move the walls into a more appropriate, expanded position to thereby increase the cross sectional area of the Eustachian tube. The balloon is then deflated into its collapsed position, and removed from the Eustachian tube.

One feature of the present invention is that it provides a method for expanding of the cross sectional area of the Eustachian tube. This feature has the advantage of helping to improve a patient's life by making it easier for the Eustachian tube to introduce air into the middle ear to help equalize the pressure between the middle ear and atmosphere. Additionally, by enabling the Eustachian tube to better drain mucus, the present invention helps to reduce the likelihood and/or severity of middle ear infections.

These and other features and advantages of the present invention will become apparent to those skilled in the art upon a review of the drawings and detailed description below, that are believed to represent the best mode of practicing the invention perceived presently by the Applicant.

IV. BRIEF DESCRIPTION OF DRAWINGS

Figure 13:
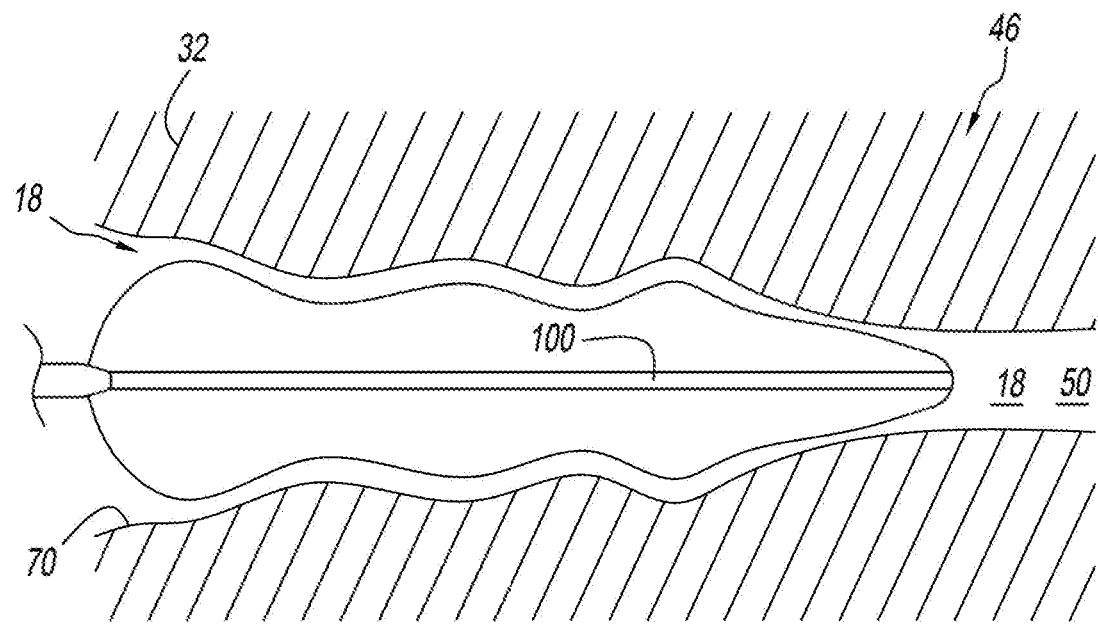
Figure 14:
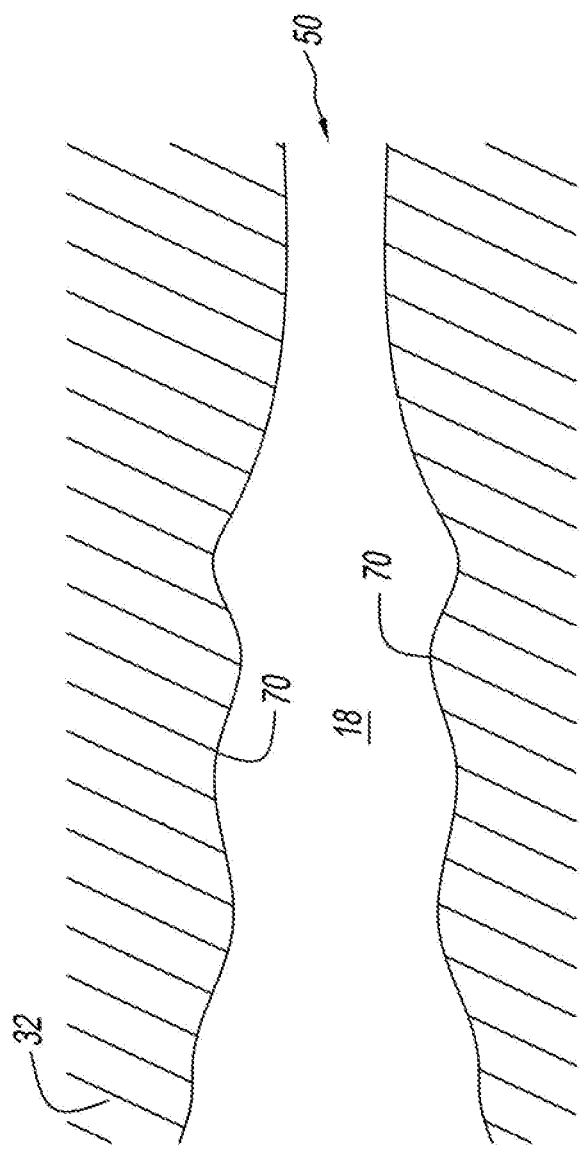

FIG. 13 is a view similar to FIG. 13, however, showing the balloon in its expanded configuration, wherein the balloon has exerted pressure against the walls of the Eustachian tube, to force the walls radially outwardly to increase the diameter of the Eustachian tube; and FIG. 14 is a side sectional view of the Eustachian tube, showing the Eustachian tube with the balloon removed therefrom, after the balloon has been inflated to "open up" and enlarge the cross sectional area of the Eustachian tube.

V. DETAILED DESCRIPTION OF THE PREFERRED EMBODIMENT

The description that follows describes, illustrates and exemplifies one or more particular embodiments of the present invention in accordance with its principles. This description is not provided to limit the invention to the embodiment or embodiments described herein, but rather to explain and teach the principles of the invention in such a way to enable one of ordinary skill in the art to understand these principles and, with that understanding, be able to apply them to practice not only the embodiment or embodiments described herein, but also other embodiments that may come to mind in accordance with these principles.

The scope of the present invention is intended to cover all such embodiments that may fall within the scope of the appended claims, either literally or under the doctrine of equivalents.

It should be noted that in the description and drawings, like or substantially similar elements may be labeled with the same reference numerals. However, sometimes these elements may be labeled with differing reference numbers, such as, for example, in cases where such labeling facilitates a more clear description. Additionally, the drawings set forth herein are not necessarily drawn to scale, and in some instances proportions may have been exaggerated to more clearly depict certain features. Such labeling and drawing practices do not necessarily implicate an underlying substantive purpose.

The present specification is intended to be taken as a whole and interpreted in accordance with the principles of the present invention as taught herein and understood by one of ordinary skill in the art.

Figure 1:
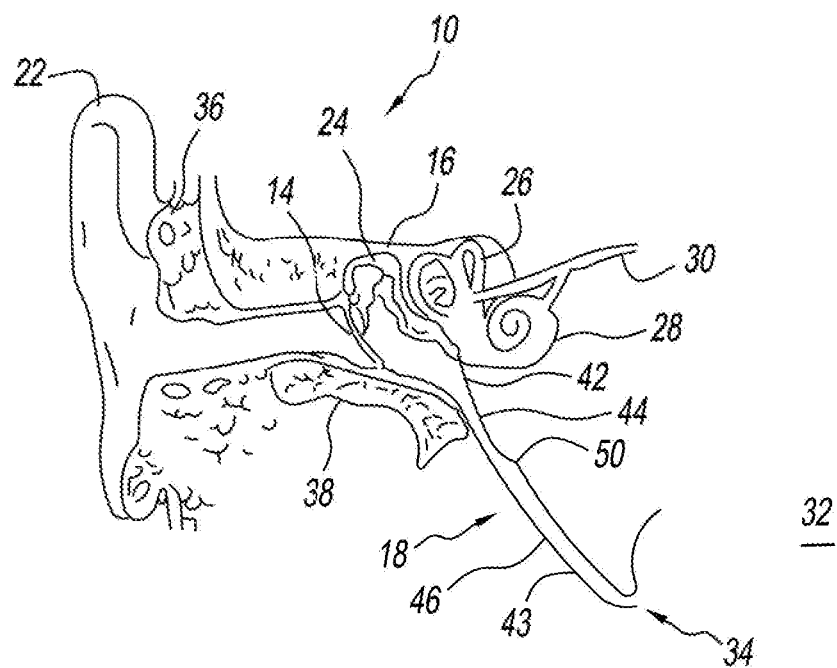
FIG. 1 is a schematic, anatomical view of the anatomy of the ear, showing the various structures and cavities of the ear, along with the airflow patterns within the ear and Eustachian tube.
Figure 2:
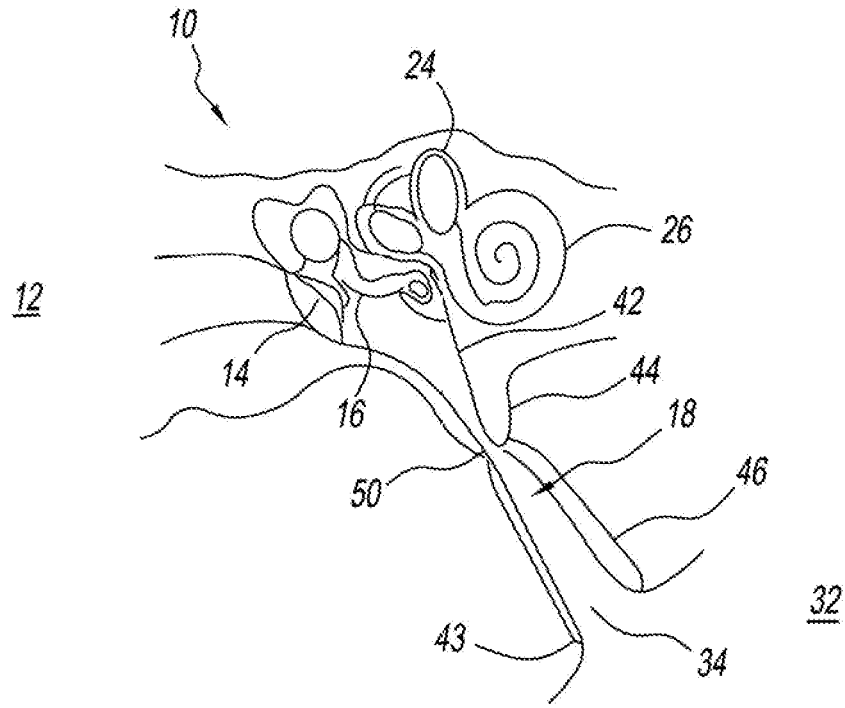
FIG. 2 is another, more enlarged, schematic model view of the Eustachian tube of the ear.
Figure 3:
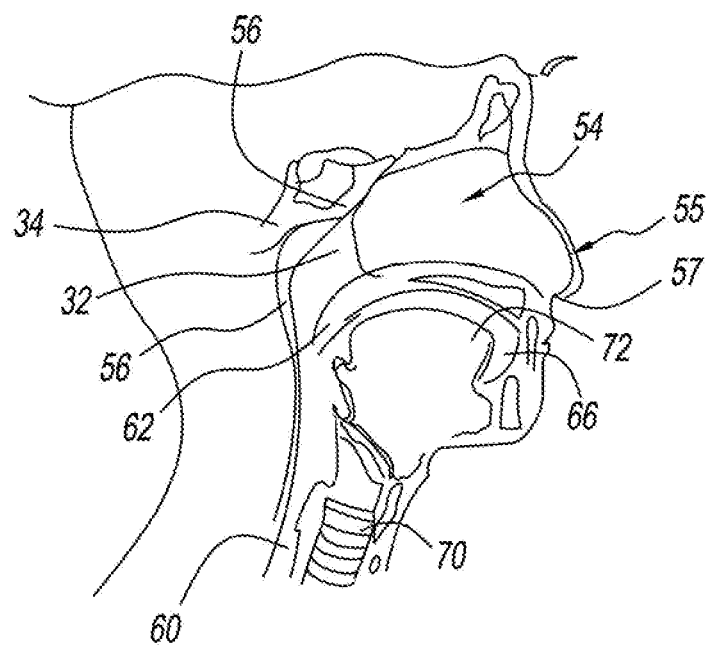
FIG. 3 is a schematic, anatomical view of the sinus cavity and oral cavity of the human, to primarily indicate the position of the Eustachian tube orifice within the nasopharyngeal cavity of the human being.

Anatomical illustrations showing the anatomy of the ear and the nasal cavity and oral cavity area are shown in FIGS. 1 through 3. The ear 10 contains a plurality of components that include the auditory canal 12 (ear canal), the tympanic membrane (eardrum) 14, the middle ear area 16, and the Eustachian tube 18.

Other ear components of interest include the pinna 22 which is the external flap that is disposed adjacent to the auditory canal 12. The ossicles 24 include the bones of the middle ear 16, including the hammer, the anvil and the stirrup. The semi-circular canals 26 are positioned in the inner ear, and help the user to balance herself. The cochlea 28 is disposed within the inner ear, and includes the portion of the ear wherein the auditory signals are converted to nerve signals, that are then transmitted though the auditory nerve 30 to the brain.

The nasopharynx also is a part of the mouth and throat cavity of the user that includes the Eustachian opening 34. Boney areas 36, 38 are disposed above and below the auditory canal 12, and help to protect the inner ear structures from damage.

As best shown in FIG. 2, the Eustachian tube 18 includes a lateral end portion 42 that is disposed adjacent to and in fluid (gaseous) communication with the middle ear 16, and a medial end portion 42 that includes the Eustachian tube opening 34 and is in fluid (gaseous) communication with the nasopharynx 32. The medial portion 43 of the Eustachian tube 18 includes a boney portion 44, as the Eustachian tube 18 is defined by generally boney tissue that defines a passageway-like cavity that comprises the Eustachian tube 18. The medial end portion 43 of the Eustachian tube 18 comprises the cartilaginous portion 46, as it is surrounded by cartilage, as opposed to the boney portion 44. The isthmus 50 is also known as the boney-cartilaginous juncture 50, and comprises the portion of the Eustachian tube 18, where the boney portion 44 meets the cartilaginous portion 46. The isthmus 50 also usually has a smaller cross sectional area than either the boney portion 44 or the cartilaginous portion 46.

Turning now to FIG. 3, the nasal, aural and laryngeal structures of the body are shown. These structures are important because of the fluid and gaseous communication between the nasal cavity 54, nose 55, nostrils 57 and the Eustachian tube 18, and also because the balloon 100 of the present invention is usually inserted through a delivery catheter guide 68 that is inserted through the nostrils 57 and into the nasal cavity 54, and then into the nasopharynx 36, through the Eustachian tube opening 34, into the Eustachian tube 18. The structure includes the nasal cavity 54, and the adenoids 56 that are disposed posteriorly of the nasal cavity 54. The pharynx, which is the area of the nasal cavity that joins to the throat includes the upper section, which is the nasopharynx 36, the middle portion which is the oropharynx 58 and the lower portion that is the laryngopharynx 60. The laryngopharynx 60 is disposed adjacent to the larynx 70. The oral cavity 64 is disposed below and anteriorly of the nasal cavity 54, and includes the tongue 72, the hard pallet 74 and the soft pallet 62.

In order to produce sound, sound waves travel through the air within the auditory canal 12, and cause the ear drum 14 to vibrate similarly to the way in which a drum head vibrates. The vibrations initiated by the ear drum 14 cause further vibrations of the middle ear components (the ossicles) 24, that ultimately result in a nerve response within the cochlea 28, that transmits nerve impulses to the brain through the auditory nerve 36. The brain "reads" these nerve impulses as hearing and sound.

The ear drum 14 extends transversely in the auditory canal 12 and separates the outward auditory canal 20 from the middle ear 16. The middle ear 16 is also an air-filled cavity. The middle ear 16 is in gaseous and liquid fluid communication with the Eustachian tube 18.

In order for the ear to operate properly, air pressure on both sides of the ear drum 14, (the auditory canal 12 side and middle ear 16 side) should be equal. In order for air pressure to be equalized, the Eustachian tube 18 is movable between a closed position and an open position. In the open position, the Eustachian tube 18 can allow air to flow from the nasopharynx 36 into the middle ear 16 to equalize air pressure on both sides of the ear drum 14. Normally, however, the Eustachian tube 18 is maintained in a closed position.

Another function serviced by the Eustachian tube 18 is that it allows mucus to drain down the Eustachian tube 18, and into the nasopharynx 32. If mucus is not allowed to drain properly, infections will grow in the mucus and the mucosa membranes of the Eustachian tube 18. These infections result in ear aches that are particularly likely to affect young children. Young children are more likely to be affected than older adults, since young children have smaller Eustachian tubes 18 that are less vertically oriented, and thereby do not drain as well as adult Eustachian tubes 18. Additionally, Eustachian tubes 18 in children often have a much smaller diameter that makes them less likely to be able to drain mucus appropriately.

Another affliction that affects certain individuals is an improperly formed Eustachian tube 18. Although deformities can take a variety of manifestations, one typical deformity is that the Eustachian tube 18 of the affected person is formed to have a smaller than appropriate cross sectional area. A person having a reduced cross sectional area containing Eustachian tube 18 is likely to suffer the same ailments as an infant, due to the reduced ability of the smaller Eustachian tube 18 to drain mucus therefrom.

As best shown in FIG. 2, the Eustachian tube 18 generally does not have a constant diameter along its length. Rather, the Eustachian tube 18 has a shape that is similar to a pair of opposed cones. The boney portion 44 has its greater diameter at its lateral end, and the cartilaginous portion 46 has its greater diameter near its medial end. The narrowest portion of a normal Eustachian tube is at the juncture 50 of the boney portion 44 and the cartilaginous portion 46 in an area referred to as the isthmus 50. As such, one might suggest that the Eustachian tube 18 has something of a "double funnel shape," as opposed to a cylindrical shape.

Figure 8:
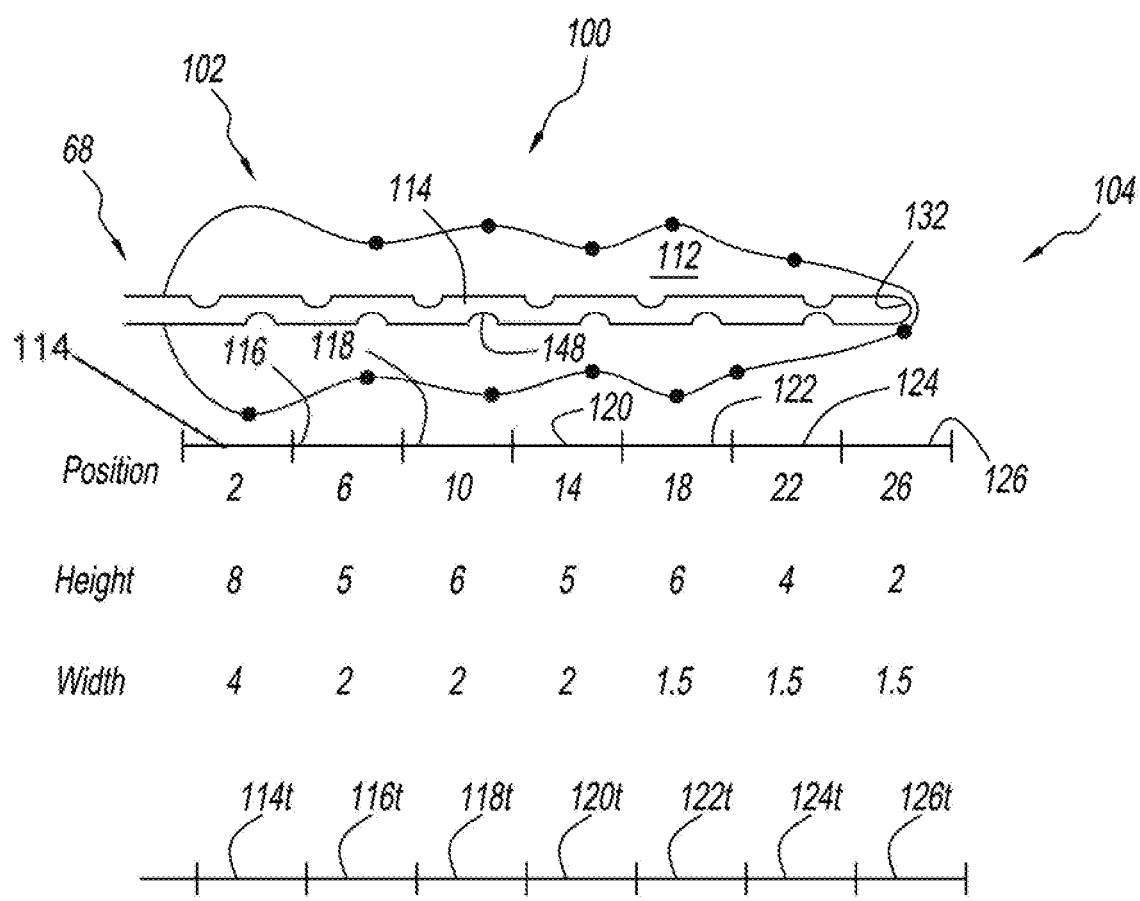
FIG. 8 is a side view and accompanying table for illustrating the cross-sectional area of the balloon of the present invention along its length.
Figures 10, 11:
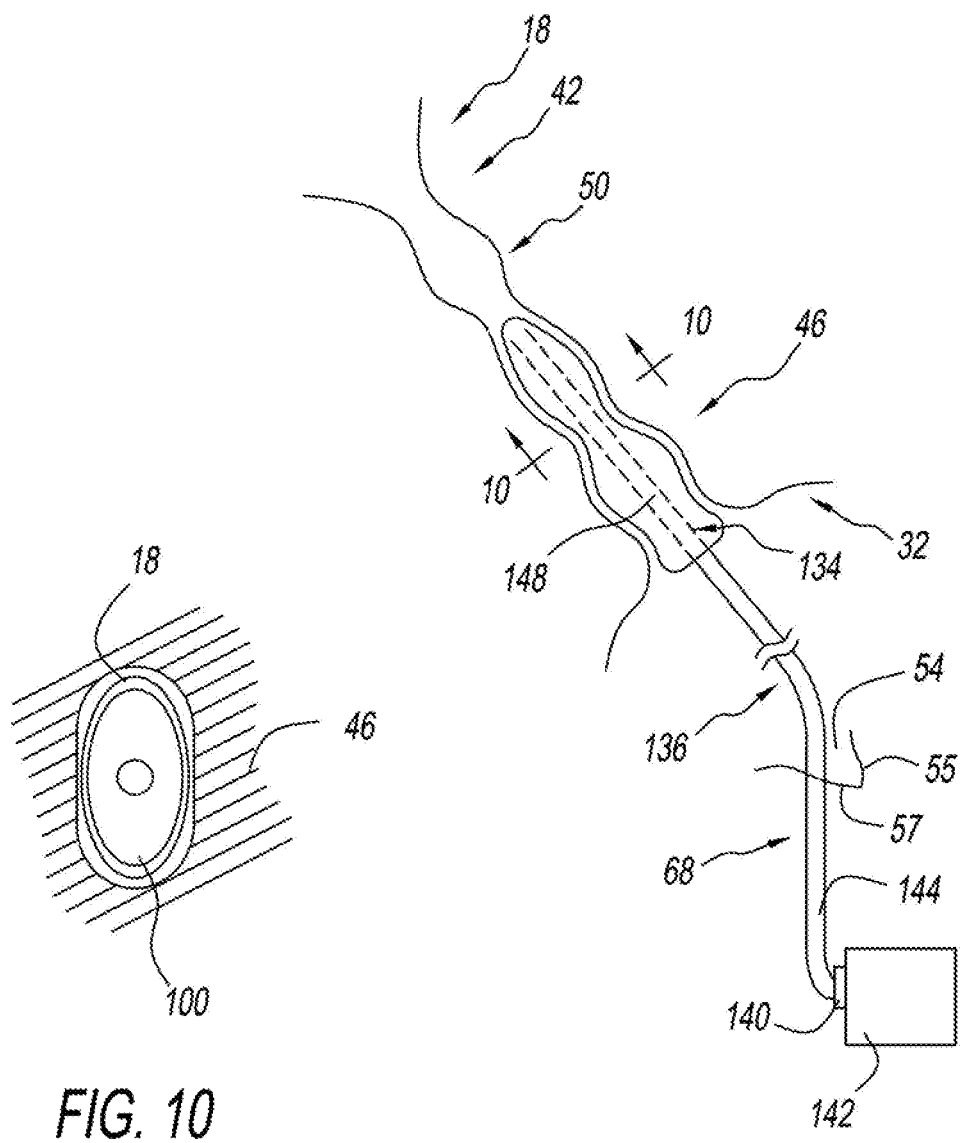
FIG. 10 is a sectional view taken along lines 10-10 of FIG. 11.
FIG. 11 is a side, sectional schematic view showing the balloon as being inserted in a Eustachian Tube, and being coupled to a guide member that is coupled to an air source.

Additionally, the Eustachian tube 18 does not have a circular cross-sectional area. Rather, the cross-sectional area of the Eustachian tube is more elliptical in shape, having a height dimension that is greater than its width dimension as shown in FIGS. 8 and 10.

A balloon 100 for insertion into a Eustachian tube 18, that is capable of opening up and enlarging the Eustachian tube 18 is shown in FIGS. 4-14. The balloon 100 includes a proximal end 102 and a distal end 104. In use, the proximal end 102 is positioned adjacent to the nasopharynx 32 (medial) end of the Eustachian tube 18 and the distal end 104 is positionied adjacent to the isthmus 50 of the Eustachian tube 18.

The balloon 100 is preferably a high pressure balloon. A high pressure balloon is a non-elastic dilation balloon that is capable of applying force against the walls 70 of the Eustachian tube 18. High pressure balloons such as the balloon 100 of the present invention are molded to their inflated geometry from non-compliant or low compliant materials that retain their designated size and shape even under high pressure.

The balloon 100 of the present invention is preferably thin walled, and exhibits a high tensile strength, with relatively low, elongation, or radial expansion. The high pressure balloon 100 preferably has a controllable or repeatable size in order to ensure that the balloon does not continue to expand past its desired size and shape, and damage or rupture the Eustachian tube 18 after opening it up to a desired cross sectional area.

The term "balloon compliance" is used to describe the degree to which the diameter of a high pressure balloon, such as the balloon of the instant application changes as a function of pressure. For example, a low compliance, high pressure balloon 100 of the present invention might be designed to expand only five or ten percent when inflated to the rated pressure. Alternately, a high compliance, high pressure balloon 100 may be used with the present invention that may stretch 18 to 30%.

These figures should be contrasted with low pressure elastomeric balloons, that are inflated by volume and not pressure. These low pressure elastomeric balloons can typically stretch between 100 to 600%. When the pressure is released from a low pressure balloon, they typically shrink back to almost their original size and shape.

Currently, most high pressure balloons, such as the balloon 100 of the present invention, are made from either PET or nylon. PET may be chosen because it offers advantages in tensile strength and maximum rated pressure, whereas nylon is softer.

The balloon 100 of the present invention should have a rated pressure of somewhere between two and twenty atmospheres (from 30 to 300 psi). Additionally, the balloon 100 of the present invention can have a coating applied thereto. A coating may be applied to alter or enhance the properties of the balloon 100 to meet the requirements. Examples of such coatings include formulations designed to modify lubricity (both hydrophilic and hydrophobic coatings), abrasion and puncture resistance, conductivity, thrombogenicity, drug release and reflectivity among other characteristics.

Additional information about the types of balloons that are used in other medical applications is contained in Mark A Saab, "Applications of High Pressure Balloons in the Medical Device Industry", *Medical Device and Diagostic Industry Magazine*, September 2000. The disclosure of this Saab article is fully incorporated herein by reference.

Figure 4:
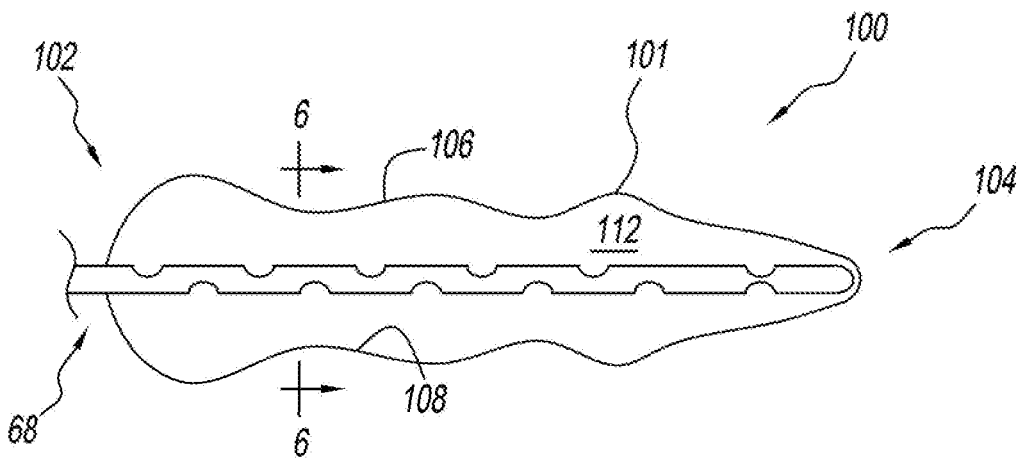
FIG. 4 is a side view of a balloon of the present invention showing the balloon in an expanded or inflated position.
Figure 5:
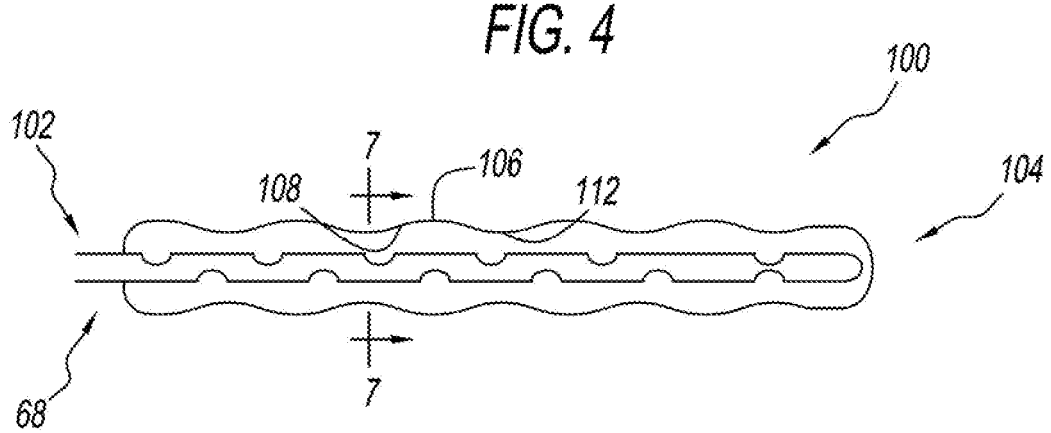
FIG. 5 is a side view, similar to FIG. 5 of a balloon of the present invention, showing the balloon in the collapsed position.

The balloon 100 is insertable into the mammalian Eustachian tube 18 as shown in the figures. The balloon 100 comprises a high pressure balloon as described above that has a body 101 that includes a proximal or medial end 102, and a lateral or distal end 104. The body 101 also includes an exterior surface 106 and an interior surface 108. The interior surface 108 defines an air receiving interior 112 that is preferably air tight. Air under pressure is inserted into the ear receiving interior 112, to move the balloon 100 between its collapsed position as shown in FIG. 5 and its expanded position as shown in FIG. 4.

A guide member catheter 68 is fixedly coupled to the balloon 100 in an air tight relation. The guide catheter 68 includes a proximal end portion 130 that is disposed exteriorly of the balloon 100, and a distal end 132 that is disposed within the interior 112 of the balloon 100. The guide catheter 68 also includes a balloon engaging portion 134 that extends generally axially along the interior of the balloon 100, and extends between the proximal and distal ends of the balloon 100. The balloon engaging portion 134 of the guide member 68 includes a proximal coupling 140 at its proximal end 130. The proximal coupling 140 is coupled to an air source 142. The air source 142 is in fluid and gaseous communication within interior air conducting passageway 144 that extends axially interiorly within most of the length of the guide catheter 68. The interior air conducting passageway 144 terminates in a plurality of apertures 148 that are disposed within the interior 112 of the balloon 100. Air can flow through the apertures 148 to place the air into air conducting passageway 144 in fluid and gaseous communication with the interior 112 of the balloon 100.

Figure 9:
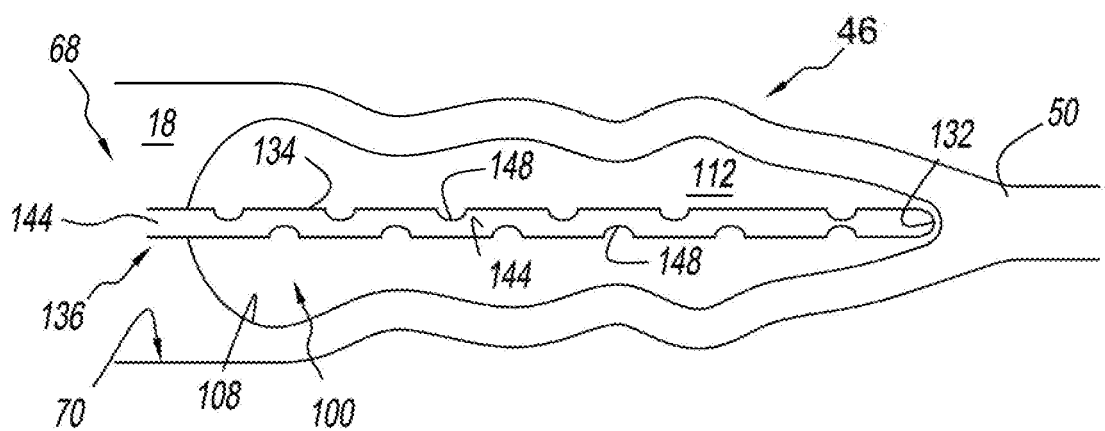
FIG. 9 is a side schematic view showing the balloon of the present invention inserted into a Eustachian tube of a patient.

Air under pressure can be forced through the interior air conducting passageway 144 and outwardly of the apertures 148, to move the balloon between its deflated and inflated configuration, such as the inflated configuration shown in FIG. 9. Alternately, the air source 142 can be operated to turn off the flow of high pressure air into air conducting passageway, or, alternately, to provide a vacuum, so that air may be withdrawn from the interior 112 of the balloon by passing through the apertures 148 and into the interior passageway 144, and ultimately the air can flow proximally toward the air source or some sort of "dump valve" to release the pressure within the interior air conducting passageway 144 and balloon interior 112. Preferably, the air source 142 is capable of exerting an appropriate vacuum, to help "suck" the body 101 of the balloon 100 radially inwardly, to facilitate its collapse, and thereby facilitate the reduction of its radial cross sectional area, to better facilitate the removal of the balloon 100 from the Eustachian tube 18.

As best shown in FIG. 9, the Eustachian tube is not shaped like a regular cone. Rather, the cross sectional area and cross sectional profile vary along the length of the Eustachian tube 18, or at least that portion of the Eustachian tube between the nasal pharynx 32 and the isthmus 50.

As shown on the exemplary Eustachian tube 18 and balloon 100 of FIGS. 8 and 9, the Eustachian tube 18 and balloon 100 are dividable up into a plurality of corresponding segments.

The segments of the hypothetical Eustachian tube 18 that are shown in FIG. 9 include (moving proximally to distally) first Eustachian tube segment 114T, second segment 116T, third segment 118T, fourth segment 120T, fifth segment 122T, sixth segment 124T and seventh segment 126T.

It will be noted that these Eustachian tube segments 114T-126T correspond in general longitudinal position with corresponding segments of the balloon 100, that include (moving proximally to distally) first balloon segment 114, second balloon segment 116, third balloon segment 118, fourth balloon segment 120, fifth balloon segment 122, sixth balloon segment 124 and seventh balloon segment 126.

Turning now to the chart below the drawing of the balloon in FIG. 8, the longitudinal position is given, along with the height and width (all in millimeters) for an exemplary, hypothetical balloon 100. It will be noted that in the hypothetical example, the height of the balloon varies from a maximum of about 8 mm adjacent the proximal end 102, to its narrowest portion of about 2 mm adjacent to the distal or lateral end 104.

The width dimension is given in the bottom line in millimeters. There are two things to note about the width measurements. First, the width measurements are generally smaller than the height measurements, indicating that the Eustachian tube is generally taller than it is wide. Additionally, there may not be any necessary correspondence between the change of size of the height, when compared to the change in size of the width. For example, the height of the second segment is five millimeters with a width of 2 millimeters. The third segment however has a larger height of 6 millimeters, but retains the same width of 2 millimeters.

It is also important to note that the cross sectional area is neither conical nor does it decrease in a linear manner wherein the cross sectional area decreases in a constantly decreasing manner. For example, a relatively proximally disposed second segment 116T has a height of five millimeters and a width of two millimeters. The relatively more distally disposed third segment 118T however, has a larger cross sectional area, as it has a height of six millimeters and a width of two millimeters.

Further, the height of the fifth segment 122T is greater than the height of either the second 116T or fourth 120T segments, although the fifth segment 122T is disposed distally of both the second 116T and fifth 122T segments.

The general dimension of the segments 114T-126T of the Eustachian tube correspond generally in size and cross sectional profile, including height and width to the size cross sectional area, cross sectional profile, height and width of the corresponding segments 114-126 respectively of the balloon 100. The segments correspond most closely after the balloon 100 has been inflated to exert its pressure to expand the Eustachian tube 18, after the balloon 100 has exerted a force against the Eustachian tube 18 to expand it to its desired configuration and diameter.

Figure 12:
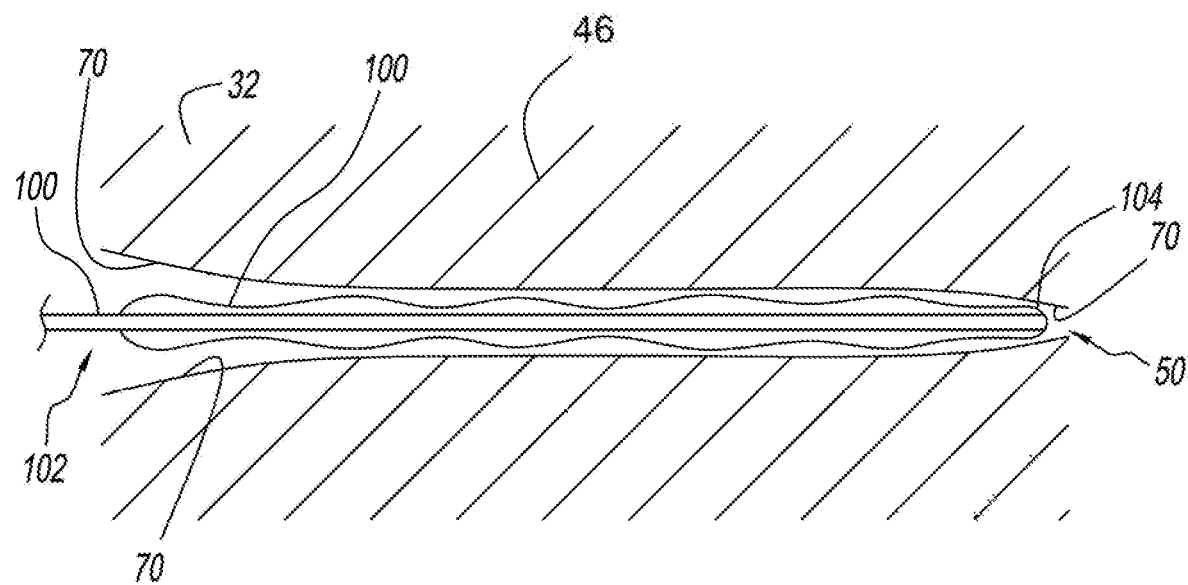
FIG. 12 is a side view illustrating a balloon of the present invention inserted into an appropriate axial position within the Eustachian tube, wherein the balloon is shown in its collapsed configuration and the Eustachian Tube is shown in its deformed configuration.

When the balloon is in its collapsed position, as shown in FIG. 12, the segments of the balloon 114-126 and Eustachian tube 114T-126T may not correspond as closely.

When inserted into the Eustachian tube 18, the medial (proximal) end 102 is disposed closer to the nasopharynx 32 and the lateral (distal) end 104 is positioned closer to the middle ear 16. As will be noted, the balloon 100 is not generally cylindrical in shape. Rather, the balloon 100 more closely follows the natural, normal contours of the Eustachian tube, such that the balloon has a generally greater cross sectional area adjacent to its proximal end 102, and a relatively smaller cross sectional area adjacent to its distal end 104. Additionally, the balloon has an elliptical cross sectional area (FIG. 6), having a "height" dimension H that is significantly greater than the width dimension W of the Eustachian tube.

Figure 6:
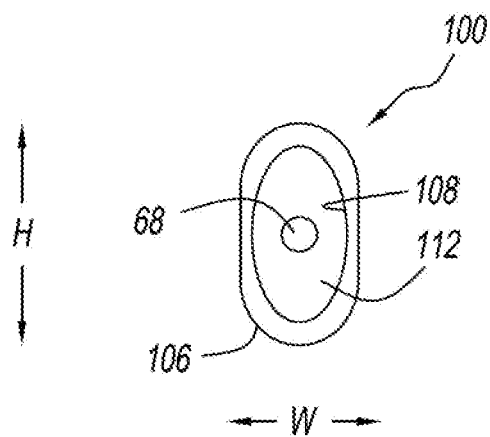
FIG. 6 is a sectional view taken along lines 6-6 of FIG. 4.
Figure 7:
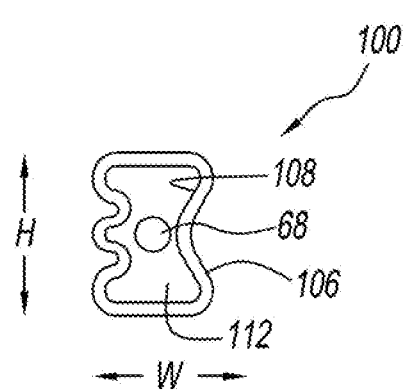
FIG. 7 is an enlarged sectional view taken along lines 7-7 of FIG. 6.

An air inlet 150 is formed at the proximal end of the balloon. The guide member catheter 68/guide member 68 is coupled or integrally formed with the air inlet 150, so that the physician can introduce air into the interior 112 of the balloon 100, and also, retract or remove air from the interior 112 of the balloon 100. As shown in FIGS. 4 and 5, the balloon 100 is moveable between a collapsed position as shown in FIG. 5, wherein the balloon has a relatively reduced diameter along its length, to an enlarged or inflated position, as shown in FIG. 4. As will be noted in FIG. 4, the cross-sectional area of the balloon 100 when inflated is significantly greater than the cross-sectional area of the balloon 100 when in the collapsed position shown in FIG. 7. In this regard, it should be noted that FIGS. 6 and 7 are not drawn precisely to scale.

The balloon 100 has a sufficiently inelastic body 101, so that the body 101 will expand to permit the balloon to move from its collapsed position (FIG. 4) to its expanded position (FIG. 4) when air is introduced into the balloon, but will only allow the balloon to expand to a pre-determined size and shape. Once this pre-determined size and shape is reached, the balloon 100 will not preferably expand any further, even if the balloon 100 is pressurized to up to 16 atmospheres of air.

The balloon 100 of the present invention is dimensioned to conform to the appropriate and correct size and shape of the normal Eustachian tube 18. As such, the balloon 100 is designed so that it has a relatively smaller cross-sectional area in places where the Eustachian tube has a relatively smaller cross-sectional area such as segment 124, 124T; and has a relatively larger cross-sectional area 118, where the Eustachian tube 18 has a relatively larger cross-sectional area 118T.

Turning now to FIG. 8, the dimensions of an exemplary balloon 100 catheter, that is sized for a typical adult ear is shown.

In FIGS. 8 and 9 the proximal end 102 of the balloon is shown at segment one 114. As such, segment one 114 is 2 mm from the proximal end of the balloon catheter. At this point, the height of the balloon is approximately 8 mm. The corresponding segment 114T within the Eustachian tube (FIG. 9) is one wherein the width of the balloon catheter 100 is approximately 4 mm.

Moving down to the distal end, the next marked segment 116 of the balloon catheter 100 corresponds to a segment whose center is positioned 6 mm from the proximal end 102 of the balloon 100. At this point, the balloon 100 has a height of 5 mm and a width of approximately 2 mm to correspond to the fact that the Eustachian tube 18 is narrowed at this point.

The third segment 118 of the balloon 100, has a centered position 10 mm from the proximal end 102 where the height of the balloon 100 is approximately 6 mm and the width of the balloon 100 is approximately 2 mm.

The fourth segment 120 of the balloon has a center point that corresponds to a position approximately 14 mm from the proximal end 102 of the balloon catheter 100, wherein the balloon 100 has a height of about 5 mm and a width of about 2 mm.

The fifth segment 122 of the balloon 100 represents a position whose center point is approximately 18 mm from the proximal end 102 of the balloon 100. At the center point, the balloon 100 has a height of about 6 mm, and a width of approximately 1.5 mm.

The sixth segment 124 has a center point approximately 22 mm from the proximal end 102 of the balloon 100, wherein the balloon 100 has a width of approximately 1.5 mm, and the balloon 100 has a height of approximately 4 mm when fully inflated. The distal end 104 segment 126 of the balloon 100 is shown as having a center point 34, that is approximately 26 mm from the proximal end 102 of the balloon 100. At this particular point, the cross-sectional area of the balloon is at its smallest, and is approximately 2 mm in height and about 1.5 mm in width.

In summary, it will be noted that the tapering of the balloon 100 corresponds generally to the tapering of the Eustachian tube 18, and that the height and width, while both tapered, may taper at different rates. As discussed above, the balloon 100 is generally elliptical in cross sectional profile to conform with the general cross sectional profile of the Eustachian tube 18, which is also somewhat elliptical, or at least, has a width that is smaller than its height (FIG. 10).

The balloon 100 is designed not only to conform to the general shape of the Eustachian tube 18, but also the general size of the Eustachian tube 18. As will be noted, the balloon 100 has a generally smaller cross-sectional area, as one moves from the proximal end 102 of the balloon 100 to the distal end 108 of the balloon, which, in the embodiment shown in FIG. 9, is 24 mm away from the proximal end 102.

The dimensions set forth in FIG. 8 are meant to be exemplary of a Eustachian tube 18 balloon 100 of the present invention that is designed to fit an average adult. In practice, is the balloon 100 of the present invention will likely be available in a variety of sizes to accommodate users having different sized Eustachian tubes 18. It is believed that this variance in size will be such that the smallest tubes used for children will be about seventy percent (70%) percent smaller than the exemplary balloon 100 of FIG. 8, and would also likely have a different shape due to the different contours of a child's Eustachian tube 18. The largest size is one that would be employed for adults having very large heads and will likely be about twenty percent (20%) larger in size than the exemplary balloon 100 of FIG. 8.

Additionally, with FIG. 8, it should be noted that the exemplary dimensions given are for the various longitudinal points along the Eustachian tube 18 starting with a point that represents the proximal end 102 of the balloon 100. When the balloon 100 is inserted into the Eustachian tube 18, the proximal end 102 of the balloon 100 is positioned generally at the nasopharynx 32 of the patient. Viewed another way, the proximal end 102 of the balloon 100 is placed at the point 34 where the Eustachian tube 18 meets the throat, which point comprises the nasopharynx 32. It is also important to note that the decrease in height and decrease in width of the balloon 100 is not a linear function. This non-linearity is caused by the fact that the decrease in height and width of the Eustachian tube 18 is similarly not linear.

In order to perform the procedure of the present invention, the balloon catheter 100 of the present invention is inserted through the nasal cavity and into the Eustachian tube 18. In order to insert the balloon 100 into the Eustachian tube 18, one inserts the balloon in its collapsed configuration through the nasopharynx 32, so that the balloon extends medially to laterally (proximally to distally) in the Eustachian tube 18. This is probably the only logical way to insert it, because if you inserted it laterally to medially, you would need to go through the ear drum 14, which would complicate the insertion and damage the ear drum 14. When properly positioned, the distal end 104 of the balloon is positioned just medially of the isthmus 50 of the Eustachian tube 18, and the proximal end 102 is adjacent to the nasopharynx 32.

Once the balloon 100 is inserted properly into the Eustachian tube 18, it is fully inflated to an appropriate pressure, through air that is provided by the air source 142, and is introduced through the air passageway 144 of the guide member 68; and then through aperture 148 into the interior 112 of balloon 100.

It is envisioned that the balloon 100 will typically be inflated to about ten atmospheres of pressure. Ten atmospheres of pressure is believed to be enough pressure to exert force against the walls of the Eustachian tube 18 in most cases to cause the cartilaginous tissue 46 in the Eustachian tube 18 to expand into its appropriate state, so that the cross-sectional area of the Eustachian tube 18 is increased.

In this regard, it is important to note that the elasticity of the tissue in the Eustachian tube varies. At some positions, the tissue of the Eustachian tube 18 is rather rigid and is formed of cartilage. At other points in the Eustachian tube, the tissue is rather more elastic and is similar to a mucus membrane.

After the balloon is inflated to approximately ten atmospheres, the balloon 100 remains in its inflated configuration for a period of approximately five minutes to continue to exert a radially outwardly directed force against the walls of the Eustachian tube 18. After five minutes, enough pressure has been exerted on the tissue for a sufficient amount of time to cause the tissue to conform and expand into whatever appropriate and desired position the surgeon so desires. To some extent, the final shape, size and position of the Eustachian tube 18 will be influenced both by the shape and dimensions of the balloon 100, and the elasticity of the particular tissue that is being deformed and reformed into its size.

After this five minute interval has passed, air can be released from the balloon 100 so that the balloon collapses back into its collapsed position. Preferably, a vacuum is pulled on the balloon to help facilitate the collapse of the balloon 100. Once the balloon collapses, it can then easily be removed from the Eustachian tube 18 and discarded. At this point, the procedure should generally be finished.

Your attention is now directed to FIG. 12. FIG. 12 shows a deformed Eustachian tube in cross-section. While looking normal, the Eustachian tube 18 is considered for purposes of this invention to be deformed, as it is narrower than is desirable. As discussed above, this narrowed Eustachian tube 18 having a smaller-than-desirable cross-section area can cause problems for the patient, due to its inability to drain mucus appropriately, and/or provide a good venting system for maintaining the pressure in the middle ear equal to that of atmosphere. Balloon 100 of the present invention is shown as being inserted into the Eustachian tube 18. The balloon 100 is in its collapsed configuration.

The balloon 100 is collapsed so that it will have a smaller cross-sectional area, to facilitate its insertion into the smaller-than-desired Eustachian tube 18. It will be noted that the proximal end 102 of the balloon 100 is disposed adjacent to the nasopharynx 32 and that the distal end 104 of the balloon 100 is disposed close to the isthmus 50.

The next progressive view is FIG. 13. At FIG. 13, the balloon 100 is shown as being inflated by introducing air into the balloon 100 from the air source 142, catheter 68, passageway 144 and aperture 148 to achieve the ten atmospheres of pressure discussed above. The inflation of the balloon 100 exerts a radially outwardly directed force against the tissue surrounding the Eustachian tube 18, to cause the cross section of the Eustachian tube 18 to expand or viewed another way, to become a larger passageway. The balloon 100 is kept within its position in the Eustachian tube 18 in an inflated configuration as shown in FIG. 13 for a period of approximately five minutes.

After the appropriate time period has passed, the balloon 100 is deflated, so that the balloon 100 returns to its collapsed configuration, similar to the collapsed configuration that is shown in FIG. 12. The balloon 100 is then removed from the Eustachian tube 18.

FIG. 14 illustrates the enlarged, re-formed Eustachian tube 118, which as will be appreciated, has a substantially greater cross-sectional area than the formerly collapsed deformed Eustachian tube 18.

Having described the invention in detail with reference to certain preferred embodiments, it will be appreciated that variations and modifications exist within the scope and spirit of the present invention.

What is claimed:

1. A balloon for insertion into a mammalian Eustachian tube, the balloon comprising:
    a high pressure balloon having a body having a predetermined designed size and shape when inflated, the body including a proximal end, a distal end, an exterior surface, an interior surface defining an air receiving interior, a lateral cross-sectional profile, and a longitudinal cross-sectional profile, the body having a plurality of segments of different lateral cross-sectional areas;
    wherein the balloon is inflatable between a deflated configuration and an inflated configuration, the body being capable of retaining its designed size and shape when in the inflated configuration, wherein the body includes at least five segments disposed along a longitudinal axis, wherein the at least five segments include three outwardly extending segments and two trough segments, wherein the trough segments are located between the outwardly extending segments; and
    wherein the at least five segments include a first segment and a second segment, wherein the first segment includes a first lateral cross-sectional area and the second segment includes a second lateral cross-sectional area different than the first lateral cross-sectional area, wherein the first segment includes a first height dimension and a first width dimension, wherein the first height dimension is larger than the first width dimension, and wherein the balloon is configured to uniformly expand the Eustachian tube when in the inflated configuration.

2. The balloon of claim 1, wherein the first segment includes a first height/width ratio, wherein the second segment has a second height dimension, a second width dimension, and a second height/width ratio, and wherein the second height/width ratio is different from the first height/width ratio.

3. The balloon of claim 2, wherein the at least five segments of the balloon includes a third segment having a third lateral cross-sectional area, wherein the third lateral cross-sectional area is different relative the first and second lateral cross-sectional areas.

4. The balloon of claim 3, wherein the third segment has a third height dimension and a third width dimension, wherein the first, second and third height dimensions are different than the respective first, second and third width dimensions.

5. The balloon of claim 1, wherein the first height dimension is at least twice as high as the first width dimension is wide.

6. The balloon of claim 5, wherein the lateral cross-sectional profile of the body is ova loid in shape.

7. The balloon of claim 1, further comprising a longitudinally extending guide member having a distal end disposed adjacent to the distal end of the balloon, a balloon engaging portion that extends through the balloon and out of the proximal end of the balloon, and a proximal portion having a length sufficient to include a proximal end that can be positioned exteriorly of a patient's nasal cavity when the balloon is positioned in the Eustachian tube.

8. The balloon of claim 7 wherein the proximal portion of the guide member is configured to receive an air source, and includes a passageway for conducting air to the balloon portion of the guide member, and the balloon portion includes at least one aperture for conducting air between the interior of the balloon and guide member for permitting inflation and deflation of the balloon.

9. The balloon of claim 1 wherein the balloon is configured for being inserted into the Eustachian tube that includes a first tube segment, wherein the first balloon segment is positioned for being received by the first tube segment, and a second tube segment, wherein the second balloon segment is positioned for being received by the second tube segment, and wherein the balloon is sized and configured so that the pressure exerted by the first balloon segment on the first tube segment is substantially equal to the pressure exerted by the second balloon segment on the second tube segment.

10. The balloon of claim 1 wherein the balloon is configured for being inserted into the Eustachian tube that includes a first segment, first and second side wall portions, an upper wall portion and a lower wall portion, a first lateral height dimension and a first lateral width dimension different than the first height dimension, wherein the first segment of the balloon is sized and configured to exert substantially equal pressures on each of the upper wall, lower wall, first side wall and second side wall when the balloon is inflated to its inflated configuration.

11. A balloon for insertion into a mammalian Eustachian tube, the balloon comprising:
a high pressure balloon having a body having a predetermined designed size and shape when inflated, the body including a proximal end, a distal end, an exterior surface and an interior surface defining an air receiving interior, wherein the body includes five segments, wherein when viewed along a longitudinal cross-section the five segments include three outwardly extending segments and two trough segments, the trough segments located between the outwardly extending segments, the five segments including a first segment having a first cross-sectional area and a second segment disposed distally of the first segment, the second segment having a second cross-sectional area larger than the first cross-sectional area, wherein the first segment has a first height dimension and a first width dimension, wherein the body includes an ova loid cross-sectional profile in which the first height dimension is greater than the first width dimension, and wherein the balloon is configured to expand a cross-sectional area of a Eustachian tube as the balloon is inflated, without tearing the Eustachian tube.

12. The balloon of claim 11, wherein the first segment includes a first height/width ratio, wherein the second segment has a second height dimension and a second width dimension, wherein the second segment includes a second height/width ratio, wherein the first height/width ratio is different than the second height/width ratio, and wherein the first height and first width dimensions of the first segment are different than the second height and second width dimensions of the second segment.

13. The balloon of claim 11, wherein the balloon is configured for insertion into the Eustachian tube, wherein when in the inflated configuration, the first segment of the balloon body is configured to expand a first tubular portion of the Eustachian tube, wherein the second segment of the balloon body is configured to expand the a second tubular portion of the Eustachian tube, and wherein when the balloon is in the inflated configuration the first cross-sectional area of the first segment of the balloon body has a larger magnitude than a first cross-sectional area of the first tubular portion and the second cross-sectional area of the second segment of the balloon body has a larger magnitude than a second cross-sectional area of the second tubular portion.

14. The balloon of claim 13 wherein the balloon is sized and configured to exert an outwardly directed force on the Eustachian tube, to expand the Eustachian tube when in the inflated configuration, and wherein the pressure exerted by the first segment of the balloon body on the first tubular portion is substantially equal to the pressure exerted by the second segment of the balloon body on the second tubular portion.

15. The balloon of claim 13, wherein when the balloon is in the inflated configuration the first segment of the balloon body is configured to exert substantially equal pressure on: an upper wall of the first tubular portion, a lower wall of the first tubular portion, a first side wall of the first tubular portion, and a second side wall of the first tubular portion.

16. The balloon of claim 15, wherein when the balloon is in the inflated configuration the second segment of the balloon body is configured to exert substantially equal pressure on: a second upper wall of the second tubular portion, a second lower wall of the second tubular portion, a left side wall of the second tubular portion, and a right side wall of the second tubular portion, and wherein the pressure exerted by the second segment of the balloon body on the second tubular portion is substantially equal to the pressure exerted on the first tubular portion by the first segment of the balloon body.

17. A balloon configured for insertion into a Eustachian tube, comprising:
a non-compliant high pressure balloon having a body that has a deflated configuration and an inflated configuration, wherein the body is configured to retain a designed size and a designed shape when in the inflated configuration;
wherein the body includes at least five segments disposed about a longitudinal axis, the at least five segments including three outwardly extending segments and two trough segments, wherein the trough segments are located between the outwardly extending segments, and wherein a cross-sectional profile of each of the outwardly extending segments differs from a cross-sectional profile of the other of the outwardly extending segments, wherein a first segment of the at least five segments includes a first cross-sectional profile having a first height dimension and a first width dimension, wherein the first height dimension is greater than the first width dimension, and wherein the cross-sectional profile includes an ova loid shape; and wherein the balloon is configured to apply pressure uniformly at an interior surface of the Eustachian tube when in the inflated configuration, and wherein the balloon is configured to expand a cross-sectional area of the Eustachian tube.

* * * * *